(12) United States Patent
Henneberg (10) Patent No.: US 10,914,423 B2
(45) Date of Patent: Feb. 9, 2021

(54) APPARATUS AND METHOD FOR LIQUID CONDITION ASSESSMENT FOR A MULTIMODE OPERATIONAL SYSTEM

(71) Applicant: C.C. Jensen A/S, Svendborg (DK)

(72) Inventor: Morten Henneberg, Aarup (DK)

(73) Assignee: C.C. Jensen A/S, Svendborg (DK)

( * ) Notice: Subject to any disclaimer, the term of this patent is extended or adjusted under 35 U.S.C. 154(b) by 232 days.

(21) Appl. No.: 16/078,814

(22) PCT Filed: Feb. 23, 2017

(86) PCT No.: PCT/EP2017/054166
§ 371 (c)(1),
(2) Date: Aug. 22, 2018

(87) PCT Pub. No.: WO2017/144589
PCT Pub. Date: Aug. 31, 2017

(65) Prior Publication Data
US 2019/0056061 A1    Feb. 21, 2019

(30) Foreign Application Priority Data
Feb. 23, 2016    (EP) .................................... 16156939

(51) Int. Cl.
*G01N 33/28*    (2006.01)
*F16N 29/00*    (2006.01)
(Continued)

(52) U.S. Cl.
CPC ............. *F16N 29/00* (2013.01); *F01M 11/10* (2013.01); *G01N 33/2888* (2013.01);
(Continued)

(58) Field of Classification Search
CPC .. F16N 29/00; F16N 2250/32; F16N 2250/04; F16N 2250/08; F01M 11/10; G01N 33/2888; F16H 57/0405
See application file for complete search history.

(56) References Cited

U.S. PATENT DOCUMENTS 3,526,127 A    9/1970  Sarkis
5,646,341 A *  7/1997  Schricker ............... F01M 11/10
                                                        701/34.4
(Continued)

FOREIGN PATENT DOCUMENTS

EP    2530367 A1    12/2012
EP    2749853 A2    7/2014

OTHER PUBLICATIONS

PCT/EP/2017/054166; International Filing Date Feb. 23, 2017; ISA Written Opinion dated Jun. 14, 2017; C. C. Jensen A/S (5 pages).
(Continued)

*Primary Examiner* — Xin Y Zhong
(74) *Attorney, Agent, or Firm* — Barclay Damon LLP (57) ABSTRACT

The present disclosure relates to a method and an apparatus for liquid condition assessment in a liquid lubrication system for a work system operable in at least two different modes, the method comprising measuring monitored liquid condition data, determining a current operating mode of the work system, then based on the current operating mode, selecting a corresponding model, modeling corresponding simulated liquid condition data based on the model, assessing the liquid condition by comparing the monitored liquid condition data with the simulated liquid condition data, and providing a normally distributed data set for the liquid condition assessment.

17 Claims, 7 Drawing Sheets

(51) Int. Cl.
*F01M 11/10* (2006.01)
*F16H 57/04* (2010.01)

(52) U.S. Cl.
CPC ...... *F16H 57/0405* (2013.01); *F16N 2250/04* (2013.01); *F16N 2250/08* (2013.01); *F16N 2250/32* (2013.01)

(56) References Cited

U.S. PATENT DOCUMENTS

| | | | |
|---|---|---|---|
| 6,324,899 | B1 | 12/2001 | Discenzo |
| 6,449,580 | B1 | 9/2002 | Bardetsky et al. |
| 7,581,434 | B1 | 9/2009 | Discenzo et al. |
| 8,322,200 | B2 * | 12/2012 | Brown ............... G01N 33/2829 73/64.56 |
| 2004/0128059 | A1 | 7/2004 | Kunz et al. |
| 2012/0025529 | A1 * | 2/2012 | Davis ...................... F03D 80/70 290/44 |
| 2012/0046896 | A1 | 2/2012 | Flandrois et al. |
| 2014/0130587 | A1 | 5/2014 | Von Herzen et al. |

OTHER PUBLICATIONS

PCT/EP2017/054165; International Filing Date Feb. 23, 2017; ISA Written Opinion dated Mar. 24, 2017; C. C. Jensen A/S (7 pages).
PCT/EP/2017/054166; International Filing Date Feb. 23, 2017; International Preliminary Report of Patentability dated May 17, 2017; C. C. Jensen A/S (13 pages).
PCT/EP/2017/054165; International Filing Date Feb. 23, 2017; International Preliminary Report of Patentability dated Jul. 2, 2017; C. C. Jensen A/S (13 pages).
U.S. Appl. No. 16/078,501, filed Aug. 21, 2018, nationalization of International Application No. PCT/EP2017/054165.

* cited by examiner

APPARATUS AND METHOD FOR LIQUID CONDITION ASSESSMENT FOR A MULTIMODE OPERATIONAL SYSTEM

CROSS-REFERENCE TO RELATED APPLICATIONS

This application is a national stage application pursuant to 35 U.S.C. § 371 of International Application No. PCT/EP2017/054166, filed on Feb. 23, 2017, which claims priority to, and the benefit of, European Patent Application No. 16156939.7, filed on Feb. 23, 2016. The entire contents of such applications are hereby incorporated by reference.

FIELD OF THE INVENTION

Method and apparatus for liquid condition assessment in a liquid lubrication system for a work system operable in at least two different operation modes.

DESCRIPTION OF PRIOR ART

Mechanical moving parts working together, such as gears, are lubricated to eliminate or reduce metal-to-metal wear thus ensuring machine uptime and operation predictability and prolonging machine life. In the art, this lubrication liquid is supplied by a liquid lubrication system enabling evaluation and purification of the liquid, removing for example wear debris particles generated as the machine wears down over time.

To assess the liquid, various sensors are placed to evaluate different aspects of its condition, such as large and small wear debris particles, water content and liquid degradation. Sometimes, this sensor data is then statistically analysed to produce basis for warnings and system stops, when the system traverses specific historically determined thresholds.

A system for monitoring the condition of oil contained within a gear box is e.g. described in EP2530367B1.

However, since machines work at different capacities for various situations, the liquid condition is affected differently even within the bounds of normal operation and therefore, technicians have a difficult time assessing, whether a change to liquid sensor data is prompted by a change in operation intensity only, or whether the system is drifting. Often, breakdowns and errors are prompted by changes to operation which is problematic as changes to sensor data is expected here and therefore, a different change than the ideal change may be very difficult or impossible to notice until damage is already caused to the system.

For example, for debris particles, a line graph depicting a dot for the sensor data for each second will populate a multi-"island" phenomenon, where any data point is more likely to be on an island than between them. Some islands may overlap, and some may be far between each other.

Increases in operating intensity produces for example spikes in wear debris generation, and here a derivation from previously lower values is to be expected. However, the exact expected increase in wear debris particles as well as the duration, which it takes to achieve a new stable wear debris particle generation rate, may be difficult to assess. In other words, the time it should ideally take to reach an equilibrium between particle generation and filtration is commonly incomprehensible to even a trained technician. This is caused in part by the many various variables playing a role, such as filter purity, system age, liquid age, machine work intensity, temperature and so on, concealing drifts in operating conditions which may produce long-term adverse effects to both the liquid system as well as the machine itself.

Also, when errors or drifts happen from a state of otherwise equilibrium and not during a change to operation as above, models of the art need to encompass the different data islands which obscure these drifts.

In the art, to encompass these island distributions and improve usefulness of gathered sensor data, statistical transformations are employed to attain a distribution which resembles a normal distribution more, typically using a logarithmic operation. Ideally, this produces a "camelback" distribution, where the mean value is in a local minimum surrounded by two global maxima corresponding to two islands, and where the probabilities then taper off below the lowest and above the highest of those maxima. However, while these transformations improve usefulness of the sensor data, they do not interpret the data concerning multiphase systems accurately.

For these systems, over half of all expected types of drifts may be concealed by the models since any drift from one island towards another is not realised until it has passed this island. In other words, drifts towards 'intermediate regions' require significantly longer to be recognised. The more islands present for sensing a system, the more pervasive this problem is since islands gain more 'neighbour islands' in whose direction drifting sensor data is difficult to understand.

U.S. Pat. No. 5,646,341 A describes a diagnostics apparatus for an engine oil system. Producers of motors model the expected values for each motor type in a simulated environment, and users are presented with a comparison between expected and actual oil pressure to diagnose the system. However, this cannot accurately model the effect of different environments, variance among different motors of the same type or wear over time. Further and importantly, the approximations achieved thereby have the disadvantage of being so imprecise outside certain threshold conditions that comparison becomes useless and system analysis has to be stopped.

For the above-stated reasons, there is a need for a more precise and robust liquid system condition assessment method and apparatus.

SUMMARY OF THE INVENTION

Then, it is the aim of the present invention to solve at least some of the above problems.

This is obtained by a method for liquid condition assessment in a liquid lubrication system for a work system operable in at least two different operation modes, wherein said liquid condition assessment comprises
  measuring monitored liquid condition data,
  determining a current operating modus or mode of said work system,
  based on said current operating modus or mode, selecting a corresponding mathematical model,
  modelling corresponding simulated liquid condition data based on said mathematical model,
  assessing the liquid condition by comparing the monitored liquid condition data with said simulated liquid condition data thereby providing a significantly normal distributed data set for said liquid condition assessment.

Thereby, changes to the measured value and drifts to its mean and variance can be identified and compared to expected values. This can be determined individually for any operational situation despite changing conditions. This allows detailed analysis of system condition as well as any system drifts that may hide from conventional sensor systems by only showing as a changed variance or mean.

By monitored liquid condition data is meant relevant sensor data pertaining to the condition of the liquid of the liquid lubrication system. Thus, wear debris particles, liquid degradation, water content, air content, temperature and pressure are all encompassed by the term monitored liquid condition data. These different sensor types are also collectively referred to as parameters.

These parameters are usually dependent variables, but may under certain circumstances take role as independent variables. There may be several independent and/or dependent variables for different mathematical models. For example, a first parameter being in one model a dependent variable of a second parameter may in another model be the independent variable, and the second parameter may then be a dependent variable.

By mathematical model is meant a formula. In accordance with the invention, it has been found that instead of using a single formula to predict system performance, a range of formulas can be used thus increasing precision. This is relevant, where simple polynomial functions do not model the whole operation range satisfactorily which is typically the case for example for a motor.

By modelling expected sensor data as well as monitoring it, discrepancies therebetween can be identified. Further, by using different formulas for different operating modi or modes, very accurate predictions can be made even for outlier operation modes thus extending system understanding and thereby increasing operation stability. For example, wear debris particle generation may depend in a complex, non-polynomial manner on operation speed and time.

By operating modus or mode is meant the situation in which the system works primarily relating to the intensity of the work being carried out by the machine. For example, whether the work system is turned on or off is an aspect of operating mode. In one embodiment of the invention, operating mode relates to the intensity of work performed by the work system, such as if it works at 30% capacity or 90% capacity. Further, other factors relating to the operation of the liquid system may also be comprised in the operating mode, such as outside temperature, pressure, and so on.

By work system is meant a system comprising moving parts that need to work in junction, and where contact between the moving parts is undesirable.

Examples of work systems could be machinery, where the liquid is used for lubrication and/or power transmission, e.g. on board ships or other off-shore installations, in wind turbine systems, in power generation plant systems and many other industrial machinery which are characterized by frequent changes in operating mode.

In an embodiment, the work system is gears as part of a motor. In a further preferred embodiment, the work system is located aboard a ship.

A work system could e.g. also be other work systems with a frequent change in operating mode, such as wind turbine systems or a power generation plant system.

By evaluation is meant a comparison typically between a modelled value and a measured value of the same parameter, where this evaluation may simply take the form of subtraction in some instances. Thereby, the result is a normalised value, where any derivation from zero constitutes a derivation from the expected. This allows better diagnosing of operations. In other embodiments of the invention, the evaluation may be more complicated than subtraction. For example, calculations may be adapted to compensate for differences in variance, such that different variances for different operating modes are encompassed. This may be beneficial when modelled sensor values differ greatly between two operating modes. Either the variance in the two modes is numerically similar differing thus as a percentage of their values, or their variances are percentage-wise similar and thus differ numerically which may be encompassed with the present invention.

By performing the method described above, operation modes are taken into account, whereby data may be normalised thus allowing data to emerge with useful mean values and variances allowing precise analysis of sensor data, where any change to sensed parameters can be quickly categorised as benign or harmful.

Furthermore, it allows creating models not only for the operational phases, but also for the change between operational phases which allows assessing, whether changes in operation intensity are mirrored as predicted by sensor data, or whether there is a drift occurring. For example, on decreasing operation intensity, wear debris may take an inordinate amount of time to settle into a lower equilibrium which may point to a clogged or ineffective filter. On increasing operating intensity, temperature may increase more than expected or faster than expected perhaps signalling that the quality of the lubrication is decreasing.

In an embodiment of the invention, the monitored liquid condition data comprises at least wear debris particle readings as well as operating modes. Wear debris particles are an important parameter of liquid condition In an embodiment of the invention, the monitored liquid condition data comprises liquid degradation readings, temperature readings, pressure readings, air content readings or humidity readings. These additional parameters describe different aspects of the liquid condition making each additional measured parameter useful.

In an embodiment of the invention, the liquid is an oil product. Oil is a typical lubricant and by using oil, the condition of the moving parts may be maintained over a long time. By oil product is meant any kind of oil and any composite products comprising oil, such an oil product being typically predominantly oil with additives to increase desired effects such as lubricity or durability.

In an embodiment of the invention, the at least two different operation modes comprise the work system being turned off and being turned on. For both system modes, an offline filtration system may still be operating and thus, the work system being turned off results in a substantially purified liquid. In this manner, the two operation modes with the greatest difference in their effect on the liquid condition is whether or not the work system is operating.

In an embodiment of the invention, at least two different operation modes comprise the work system being turned on. The work system may work at different intensities which may be modelled using a method according to the present invention.

In an embodiment, the liquid lubrication system is for a work system on a ship. On ships, operation stability is especially important since if equipment or a single crucial machinery stops working, the entire ship is put out of function making breakdowns extremely expensive.

The invention further relates to an apparatus for performing any of the above-mentioned functions.

LIST OF FIGURES

FIGS. 4 A-C are graphical views of data comparison according to the present invention.

DETAILED DESCRIPTION OF THE EMBODIMENTS OF THE INVENTION

In the following, embodiments of the invention will be described further.

Figure 1:
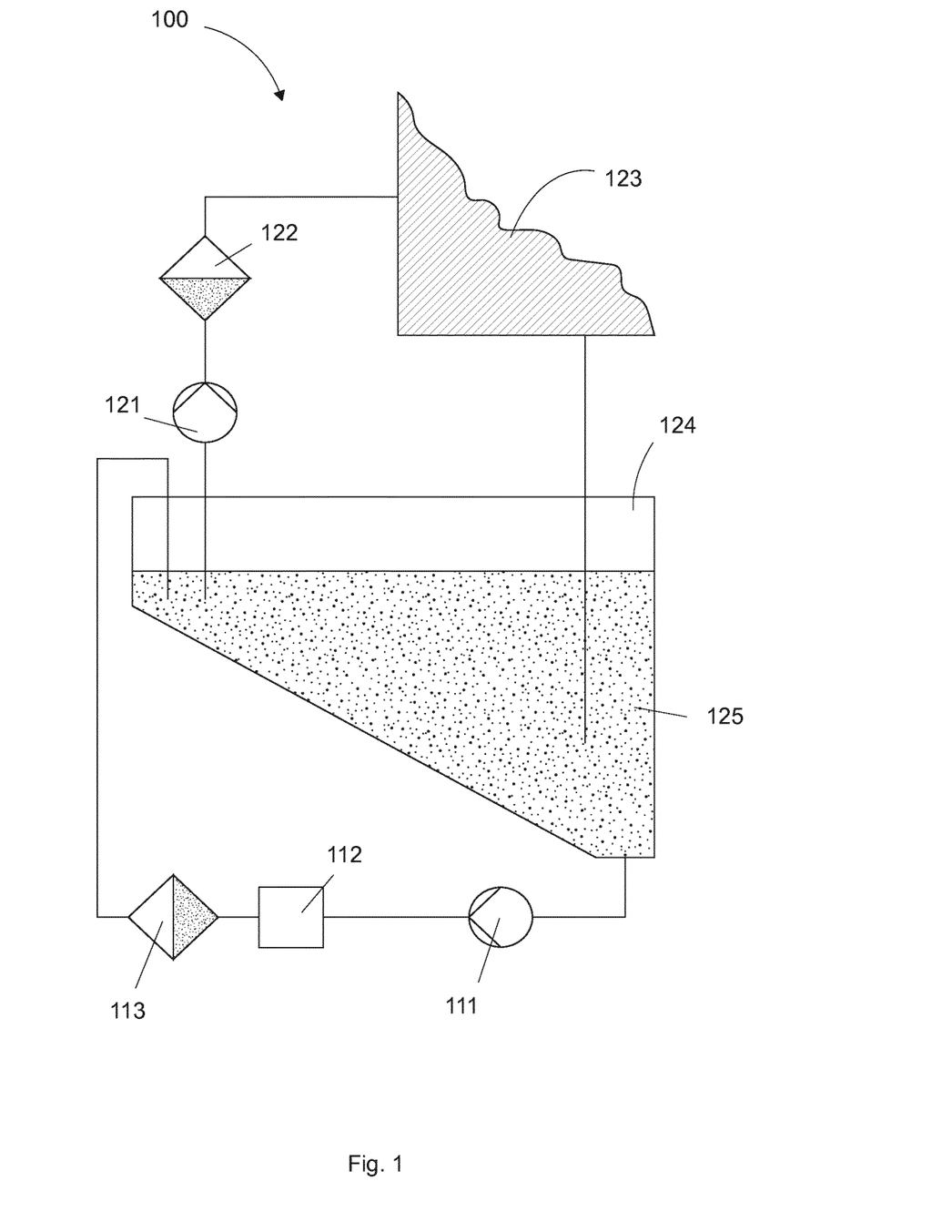
FIG. 1 illustrates a schematic view of a liquid lubrication system.

FIG. 1 illustrates a liquid lubrication system 100 for lubricating a machine 123. The system comprises an in-line lubrication system comprising an in-line filter 122 and an in-line pump 121, where the in-line pump draws lubrication liquid 125 from a reservoir 124 onto the moving parts of the machine, such as gears, thus lubricating them. This ensures that the machine parts move effectively for operation, where the in-line filter ensures that no large debris particles enter the moving parts. The machine generates wear debris particles which are carried into the liquid reservoir 124.

The system further comprises an offline system comprising an offline pump 111 and an offline filter 113, where the offline pump draws contaminated lubrication liquid, typically from the bottom of the reservoir, where it is most contaminated, through the offline filter 113, and returns purified liquid to the reservoir. The offline filter 113 is typically more efficient than the in-line filter 122, works at lower liquid velocities and is adapted to filtrate smaller particles than the in-line filter 122 which in turn do not need to exert too much resistance on the flow of the liquid. Furthermore, a parameter sensor 112 is placed somewhere in the system conveniently along the offline pipe.

The lubrication system works in at least two modes, i.e. with the machine turned on and turned off. It may operate in yet more modes, such as a variety of subsets of being turned on, for example by providing a burst of power on start-up. It may work according to a variety of intensities, such as anything between zero and one hundred percent of machine capacity. Various modes may be imagined to produce different amounts of wear debris and in other ways produce different expected sensor signals or in other words, have different mean values and variances for these signals.

When the machine is turned off, the offline system may still operate to purify the liquid thus reaching lower amounts of wear debris than during operation since during operation of the machine, a steady stream of wear debris is produced by the machine and released into the reservoir 124.

Although the embodiment of the invention described pertains to wear debris, sensed parameters may be any parameter that describes the liquid condition, conveniently at least wear debris, but may also consist chiefly or solely of liquid degradation. Furthermore, a multitude of parameters may be used, such as liquid degradation, temperature, pressure, water content and air content. The sensor 112 monitoring liquid condition may be placed anywhere within the system such as upstream from the offline filter or conveniently downstream from this offline filter 113. Since the offline filter 113 is conveniently always or substantially always in operation, placing the sensor 112 here allows steady supply of sensor data although the placement is of no consequence to the invention itself.

Figure 2:
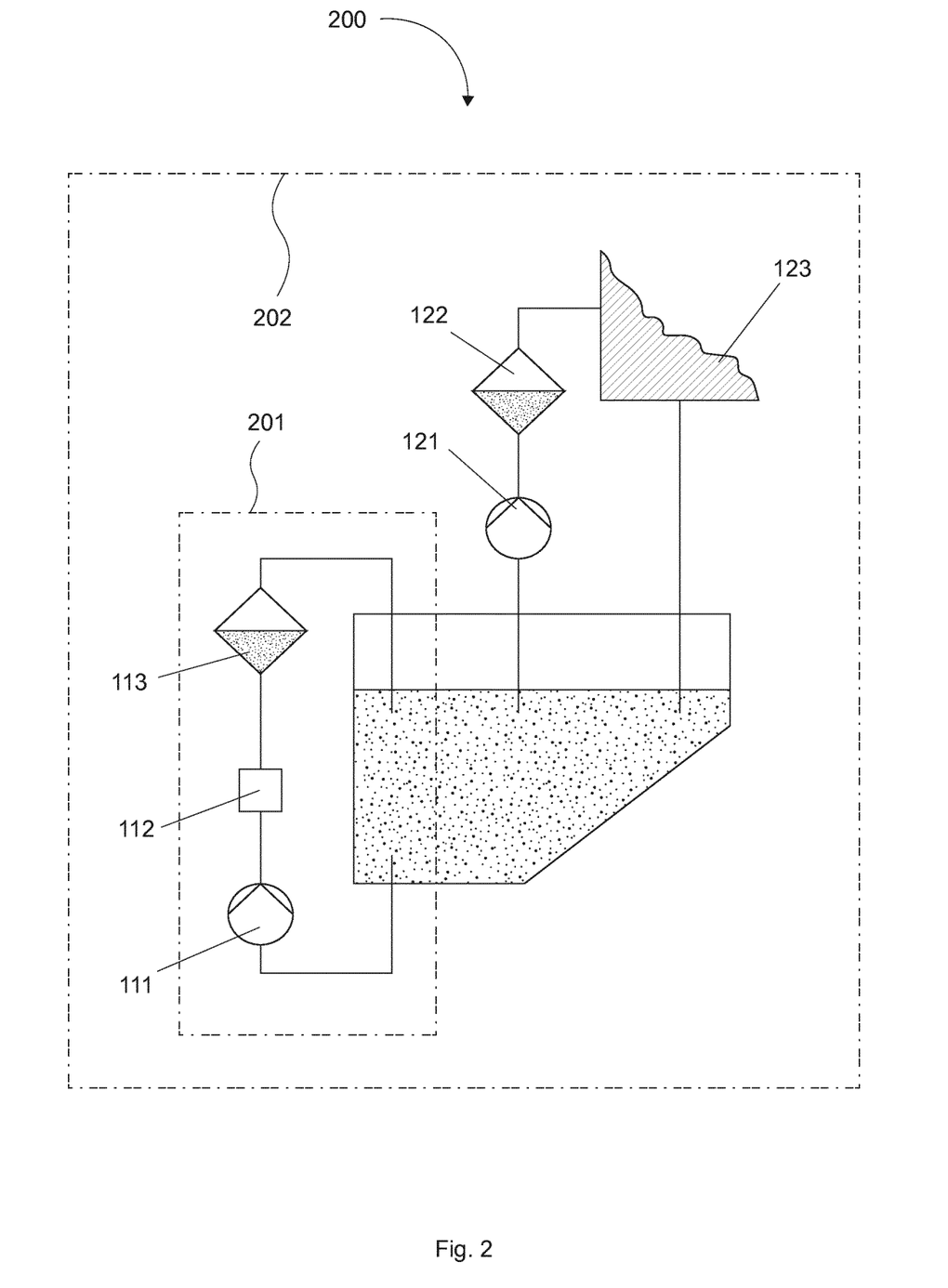
FIG. 2 is a schematic view of operating modes of a system.

FIG. 2 illustrates the elements of the lubrication system 200, where elements from two different operating modes of the system are identified. The operational modes correspond to at least a passive operation mode 201 and an active operation mode 202, where the machine is turned off in the passive operation mode, and only the offline system is active, and, the machine is turned on in the active operation mode, and the in-line system is active as well. This produces two different situations. Since in the passive operation mode, no wear debris particles are generated, the filtration performed by the offline filter purifies the liquid substantially. In the active operation mode, the machine continuously generates wear debris into the liquid which is continuously being purified by the offline and in-line filters. Over time, an equilibrium is then achieved depending on the efficiency of the two filters 113, 122 and the degree of released wear particles from the machine 123.

For each different situation 201, 202, a mathematical model specific to that operation mode describes expected parameter data. A measured value that may otherwise seem within limits is for example revealed to be harming the system, such as an excessively large amount of wear debris during the passive operation mode which may as an example be caused by ineffective or broken filters.

The mathematical model of operating modes shown in FIG. 2 is specifically schematised for wear debris although according to the present invention, other models may be developed for other sensor data sets. These models need to take into account what factors are important to the states of their values. For example, filters are likely not important for temperature, while filters may affect pressure—although not through filtration efficiency but flow resistance. Even outside parameters such as environment temperature may be important to model expected system behaviour effectively.

In FIG. 2, only two different operating modes are identified 201, 202. However, depending on the intensity of operation, the active mode 202 may vary greatly and may thus be subdivided into more nuanced operating modes, each of which will then have its own mathematical model.

Figure 3:
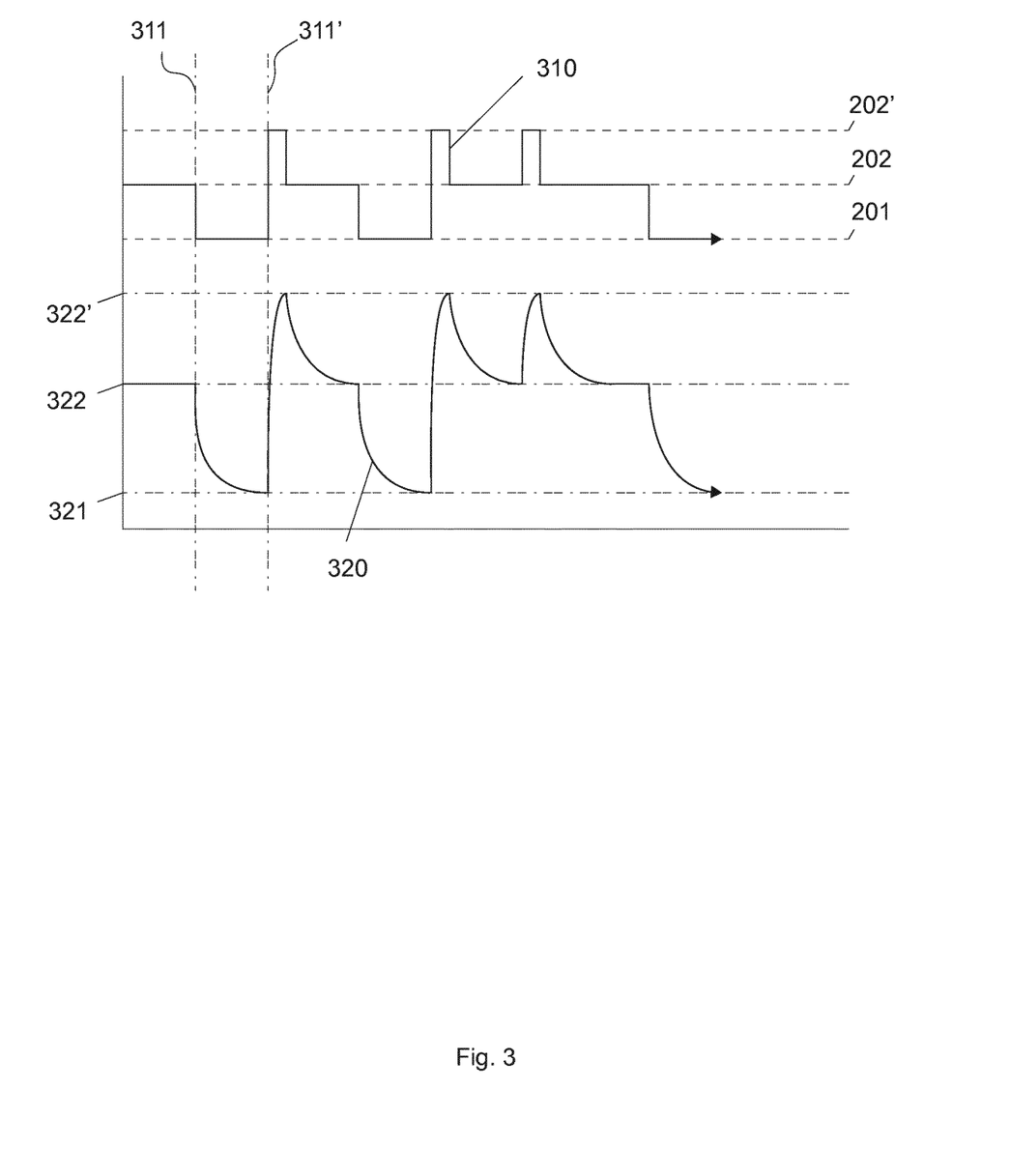
FIG. 3 is a graphical view of modelled wear debris.

FIG. 3 is a graphical view of the modelled wear debris 320 as variable of current operating mode 310. At any given time, operation intensity 310 takes one value. In the simplest embodiment of the invention, operation intensity may take two different values, for example the values of passive mode 201 or active mode 202, although in the embodiment according to FIG. 3, a third mode is further possible. i.e. burst mode 202'. In burst mode 202', the machine is active like in the active mode 202 and further, the machine operates at higher intensity. This mode is often used to start the system up, to quickly achieve a momentum which a lower intensity can then maintain. This is for example useful for propellers on ships, where starting a movement of a body in water is difficult, while maintaining one is comparatively easier.

Depending on the current operation intensity, various wear debris measurements can be expected. In the embodiment according to FIG. 3, the long-term expected measurements are substantially no wear particles 321 corresponding to a passive mode 201; normal wear particle count 322 corresponding to an active mode 202; and a high wear particle count 322' corresponding to a burst mode 202'.

Because the system requires time to adjust to new operation modes, previous sensor readings are also important in ascertaining expectable measurements as the modelled wear debris 320 develops towards equilibria corresponding to particle counts 321, 322 and 322'. Therefore, a certain feedback lag may be expected and thus, differential equations are needed to determine the trajectories of system sensor data.

This is illustrated by the curved lines of modelled wear debris 320. At a first, operation mode change 311, current operating mode 310, is shifted from an active mode 202 to a passive mode 201 instantly, where the machine is turned off. Expected parameter readings then tapers off from normal wear particle count 322 to substantially no wear particles 321 as filters filter more and more wear debris particles, but slower and slower as there is yet farther between particles.

When a second operation mode change 311' occurs, expected wear particle measurements approach high particle count 322', where the particle density is so high that the filters remove particles equaling the number added by machine wear. These changes to current operating mode 310 and its corresponding lagging change to modelled wear debris 320 continue over time.

Variables and constants needed for these formulas to work can be historically determined from the system during a run-in phase and/or based on expected values, such as by using data sheets of relevant components and/or by using reference values from other similar systems.

The system model 200 may be adapted during and after use to increase its precision. This can for example be done by either including new variables or constants, by calibrating the values of these, and/or removing variables and constants. It may also be done by including new formulas for new operation modes. For example, a system model 200 may initially comprise two formulas relating to two operation modes. After a while, a new formula may be included into the system model which may constitute another work intensity of the machine, whereby the system model comprises three formulas and its precision is thus increased.

In one embodiment of the invention, a variety of work intensities may be derived from an initial set of work intensities from which a series of formulas may be developed for the system model 200. For example, a system may be operated in 30% of machine capacity and 90% of machine capacity most of the time with small periods of time being operated anywhere in between, such as at 45% or 60%. By comparing values of constants and variables at two or more work intensities, functions may be developed for variables and constants whose values are dependent on work intensity. For example, machine wear debris generation may take one value at 30% work intensity and a higher value at 90% work intensity. By comparing the value at two or more points, variables and constants may be extrapolated for intermediate values, and formulas may be developed for any intensity in between two or more initial work intensities. In another embodiment of the invention, estimation of intermediate constant and variable values may be performed according to any function type, such as a power function or a logarithmic function by comparing at least two and conveniently at least three work intensities.

Though the shifts between steady states (states in equilibrium) are non-linear, they are mathematically deterministic meaning that they are calculable, and that systemic derivations from these curves signify system drifts which are then identifiable according to the present invention. Therefore, system drifts are discernible even during changes.

Figure 4:
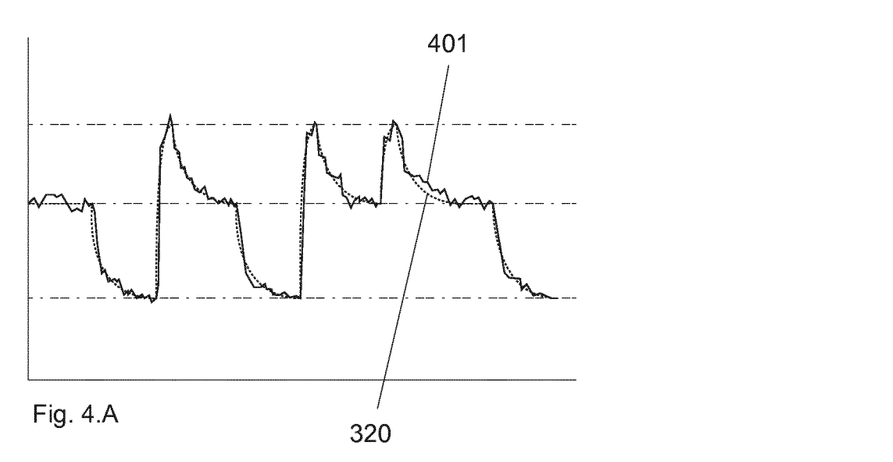

FIG. 4 illustrates a graphical correlation between sensed data and modelled data.

FIG. 4A illustrates a graph containing both modelled wear debris 320 and monitored liquid condition data 401. As can be seen, a fit is attainable, where the monitored data fluctuates around the expected data.

FIG. 4B illustrates a data set normalised based on subtracting modelled wear debris 320 and monitored liquid condition data 401. In this way, compensation is made for different operation modes, whereby normalised measurement data 402 emerges. The normalised measurement data 402 has a single mean value 403 and a variance. By thus attaining for the system a data set with a mean value and a variance, operation performance can be precisely assessed.

This allows sensitive evaluation of changes to monitored system condition parameters, where any change is evaluated against its expected value and trend.

FIG. 4C illustrates a resultant significantly, normally distributed data-set (404), where normalised measurement data 402 has been used.

Because sensor data can be trusted to a higher degree, not only errors but systemic drifts can be readily identified. When the system repeatedly attains values out of the expected, it may signify system wear. For example, water content may increase slightly but unavoidably, or events causing a significant increase in water content may become more common over time. These represent changes to the mean value and the variance, respectively.

Based on these precisely identified wear patterns, system life can be precisely projected, especially when a previous system life has been monitored against which the system can be compared.

Figure 5:
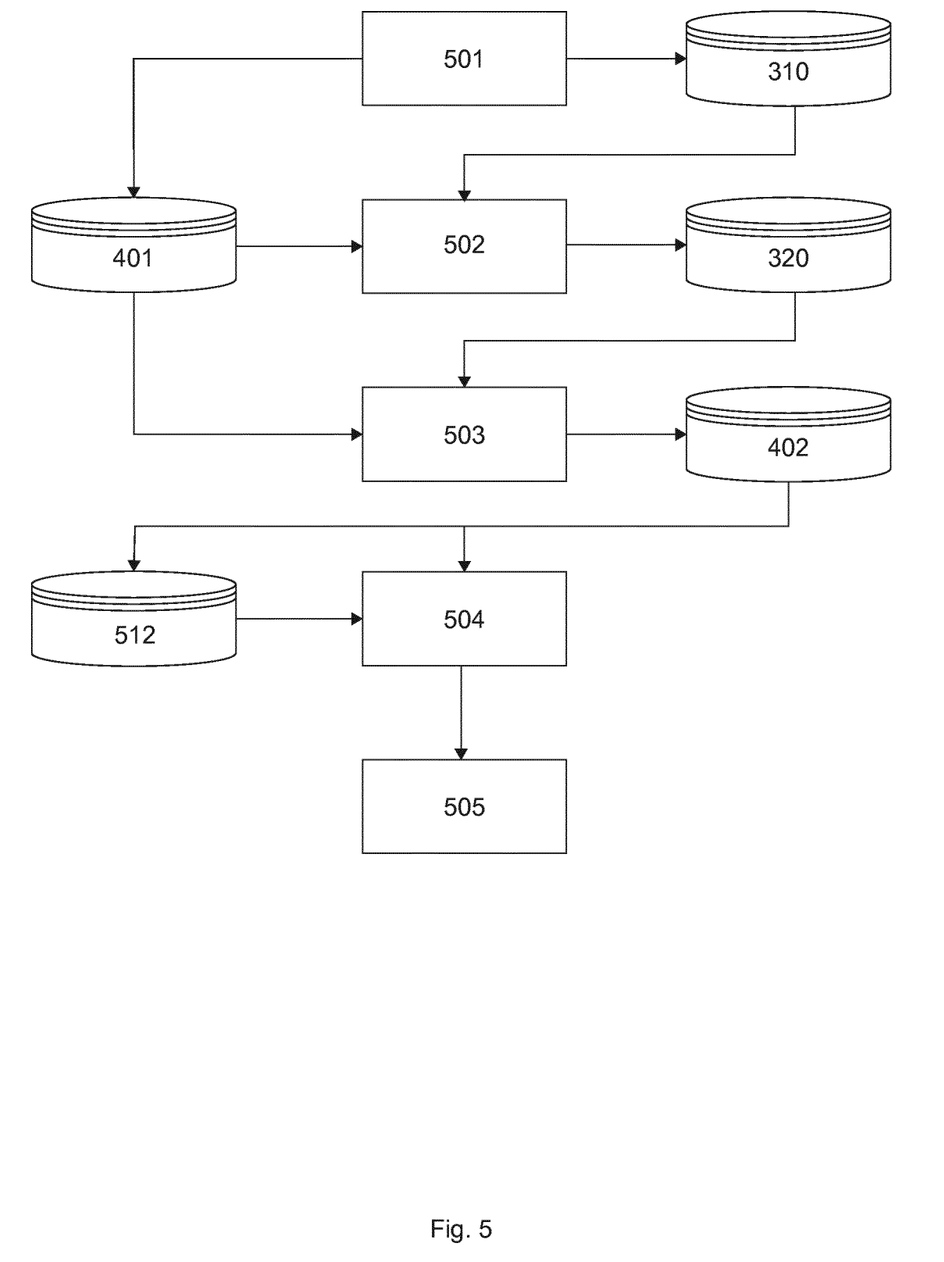
FIG. 5 illustrates a control flow according to the present invention.

FIG. 5 is a data flow according to the present invention. The cylinder-shaped boxes represent data storages, while the rectangular boxes represent processes, and lines being data flows. The data may be thought to be stored in a central or in distributed databases between being used for the processes according to the invention.

One or more sensors 112 in the system are adapted for system measuring 501. System measuring may comprise a variety of sensors and a variety of placements within the system, and system measuring is performed continuously. In one embodiment, the resultant monitored liquid condition data 401 is transmitted continuously, where continuously means that data is transmitted at least once a minute, preferably at least once every ten seconds. In one embodiment, it is important that the system transmits values at operation mode changes. Furthermore, system sensing also comprises determining the current operation mode 310.

By model usage 502, the system model 200 is used to identify the correct mathematical model to use for calculating parameter data and then to perform relevant calculations. In an embodiment of the invention, the system model comprises a list of formulas. In an embodiment of the invention, a formula for each operation mode is developed.

In another embodiment, model usage 502 comprises checking for a series of parameters in determining the most fitting formula of which current operating mode 310 may be one. Other factors, such as monitored liquid condition data may play a role as well. For example, with a high degree of air inside the system, pressure may behave very differently thus prompting the use of a formula adapted for such a situation in case pressure is the parameter being modelled. The system model 502 should optimally be adapted so that exactly one formula is identified for any given situation or alternatively, so that they are ranked for fit, where the best fit can then be selected. Conveniently, identification of the most adapted formula is performed electronically through an algorithm. Because the system is time-sensitive, previous values play a role and differential equations are useful in the system model 200.

When a suitable formula is identified, previously collected monitored liquid condition data 401 or another suitable data source is used as a base value. The identified formula is then deduced, and an expected sensor reading results therefrom.

Measurement normalisation 503 is then performed based on monitored liquid condition data 401. The modelled wear debris 320 resulting from the model calculations is compared with wear monitored liquid condition data 401, and any normalised measurement data 402 can be identified precisely.

This comparison may simply comprise subtracting the modelled wear debris from the sensed wear debris. However, more refined normalisations may be performed as well. Such a more refined normalisation may include different variances for different operating modes taken into account. For example, operation modes with higher expected values may have higher expected variances which are taken into account in the present invention.

By thus identifying normalised measurement data 402, the technician is enabled to assess, whether changes to operation mode show system drifts, or whether changes happen according to the model. Over time, drifts in equilibria may be identified as well.

Based on a period of gathered normalised measurement data 402, system reference data 512 is developed based on which subsequently normalised sensor data can be assessed. This reference data 512 is developed over a given period of time. It is not instrumental to the invention that the period itself is of a given length although a longer period supplies more accurate data. The period should not be too long either since the system is continuously being worn down, whereby a too long reference period may actually be more inaccurate than a shorter one. Conveniently, a week, a month or a year may be used to develop the reference data although when at first implementing a monitoring system according to the invention, shorter periods may be used to develop bootstrap reference data, such as an hour or a day.

In an embodiment of the invention, the reference data is continuously or regularly calibrated to reflect changes to system performance, such as reflecting system wear. For example, older liquid systems may be more susceptible to heat, whereby slight changes to operating intensity produce a hot liquid that may decrease viscosity detrimentally, thus increasing metal-to-metal wear and producing wear debris particles. The system reference data 512 is then conveniently updated to signify the detrimental effect of previously benign system changes. These calibrations also pertain to the model itself as well as its variables and constants which may change over time.

The reference data 512 takes at least the normalised measurement data 402 into account.

Because the monitored liquid condition data is normalised through the model prior to being adapted into reference data, it is substantially prepared to be probability distributed. It is a central aim of the invention to improve system understanding for the technician and therefore, probability distributing the normalised measurement data 402 is useful.

By probability distributing the reference data, later readings may be contextualised, whereby the technician may not only assess whether a given signal is as expected or not, he may also assess how unlikely any given current reading is. System condition evaluation 504 is then performed, where a current normalised measurement data 402 reading is compared to system reference data 512. This allows the technician to see the current situation in light of previous, similar situations.

In an embodiment of the invention, not only a single signal value is compared to the system reference data, but a series of the latest consecutive signal readings are compared to system reference data. This allows detrimental operation trajectories to be identified while still within normal operation.

Based on the system evaluation, a signal is transmitted which describes the state of the system and which is adapted to give warnings. It may be adapted to give early warnings.

Though the embodiment described is adapted to pertain to wear debris particles only, this is done for communicative purposes since any parameters of a lubrication liquid or liquid lubrication system may be monitored according to the present invention, such as liquid degradation, temperature, pressure, water content, air content, parameters relating to the operation of the system such as power and so on.

Figure 6:
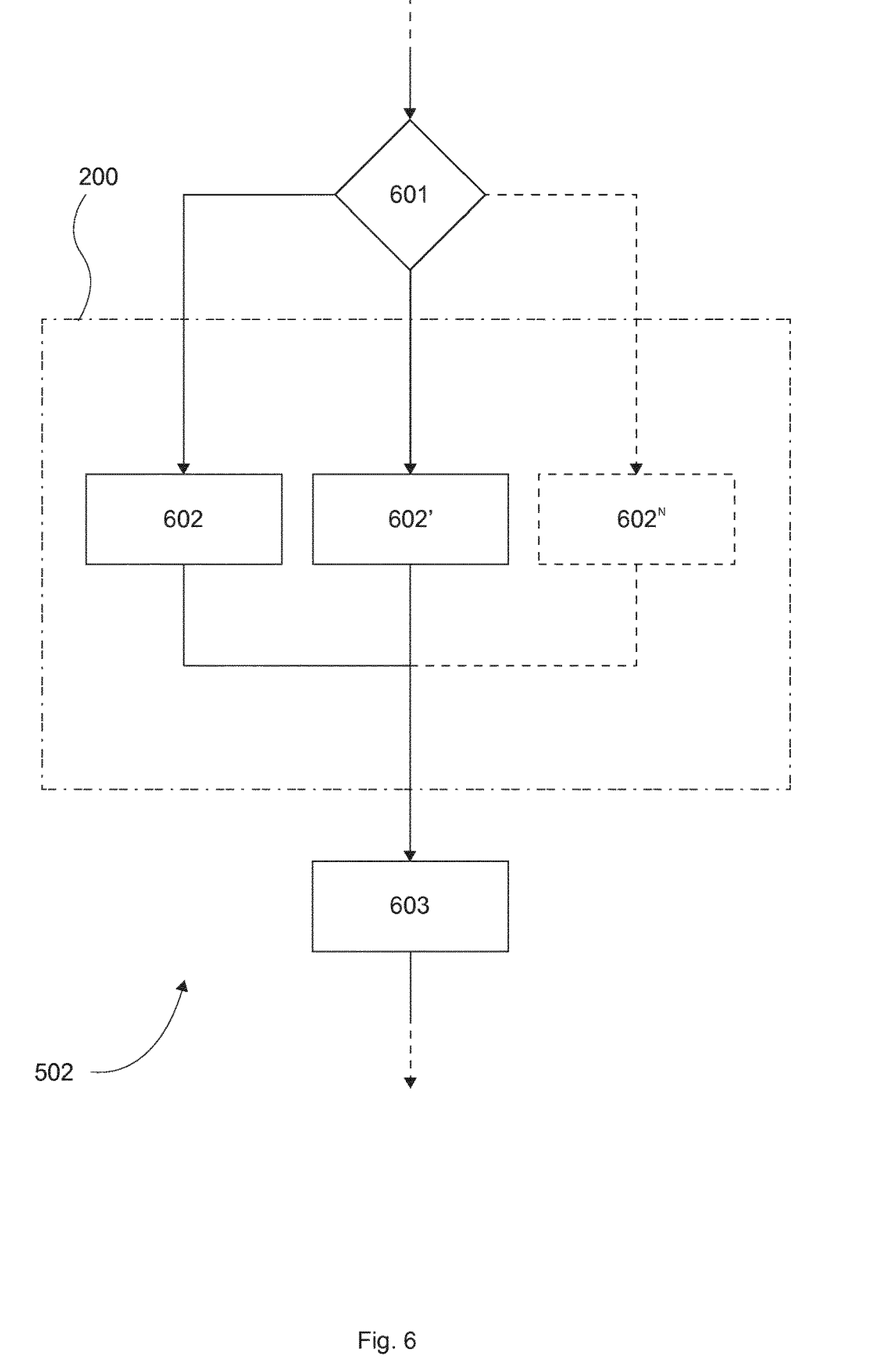
FIG. 6 illustrates graphs of a method according to the art.

FIG. 6 illustrates the steps involved in model usage 502. Monitored liquid condition data 401 is input into the process, where at least current operation mode 310 is used as well.

Conveniently, at least current operating mode 310 is used to select the most fitting mathematical models 602, 602', 602". Other data may be used in this process as well, such as certain monitored liquid condition data 401. For example, a sufficiently high air content in the system may produce drastically different behaviour for certain parameters, such as pressure. The system model comprises at least two mathematical models, and may comprise any number of mathematical models 602, 602' 602$^N$.

After the most suitable mathematical model has been selected, relevant parameters are inserted into the model, whereupon model resolution 603 is performed thus producing simulated liquid condition data 320.

Figure 7:
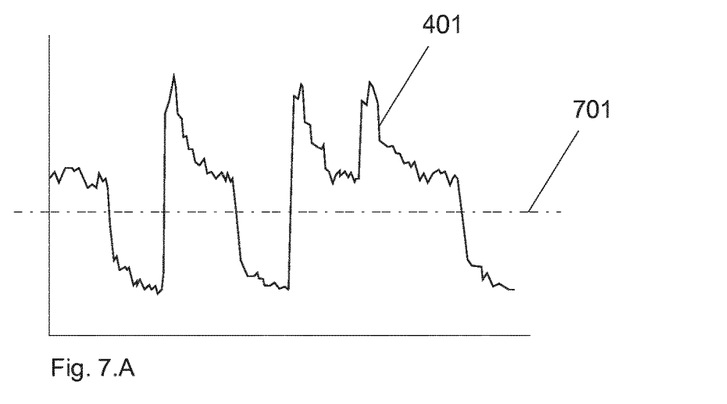
FIGS. 7A-C illustrate the approach to system diagnostics according to prior art.

FIG. 7 illustrates the approach to system diagnostics according to the art and has been included here for communicative purposes.

FIG. 7A illustrates the raw data available for analysis, the monitored liquid condition data 401, as well as its mean value 701. For systematically asymmetrical data like monitored liquid condition data 401, system drifts may easily happen within the thresholds of normal operation without it being noticeable.

Increases in operating intensity produce for example spikes in wear debris generation and here, a derivation from previously lower values is to be expected. However, the exact expected increase in wear debris particles as well as the duration, which it takes to achieve a new stable wear debris particle generation rate, may be difficult to assess. In other words, the time it should ideally take to reach an equilibrium between particle generation and filtration is commonly incomprehensible to even a trained technician. This is caused in part by the many various variables playing a role, such as filter purity, system age, liquid age, machine work intensity, temperature and so on. This conceals drifts in operating conditions which may produce long-term adverse effects to both the liquid system as well as the machine itself.

FIG. 7B illustrates a probability distribution 702 that may describe a distribution over monitored liquid condition data. Because the context of readings are not considered, a drift from a first probability island 702' towards a local minima 702" cannot be identified easily. As long as measurements remain between a first probability island 702' and a third probability island 702''', assessing system condition is difficult, and drifts remain hidden. Over half of all expected types of drifts may be concealed by the models since any drift from one island towards another is not realised until it has passed this island. The more islands present for sensing a system, the more pervasive this problem is since islands gain more 'neighbour islands' in whose direction drifting sensor data is difficult to understand.

FIG. 7C illustrates the transformations performed in the art to remedy the situation. Ideally, this produces a "camelback" distribution, where the mean value is in a local minimum surrounded by two global maxima corresponding to two islands, and where the probabilities then taper off below the lowest and above the highest of those maxima. However, while these transformations improve usefulness of the sensor data, they do not interpret the data concerning multi-phase systems accurately and are therefore unsatisfactory to assess system health despite the work they require.

REFERENCE NUMBERS

100—Liquid lubrication system
111—Offline pump
112—Sensor
113—Offline filter
121—In-line pump
122—In-line filter
123—Machine
124—Liquid reservoir
125—Lubrication liquid
200—System model
201—Passive mode
202—Active mode
202'—Burst mode
310—Current operating modus or mode
311—First operation mode change
311'—Second operation mode change
320—Simulated liquid condition data
321—Substantially no wear debris
322—Normal wear debris
322'—High wear debris
401—Monitored liquid condition data
402—Normalized measurement data
403—Mean value
404—Significantly normal distributed data-set
501—System measuring
502—Model usage
503—Measurement normalization
504—System condition evaluation
505—Signal handling
512—System reference data
601—Model selection
602—First model
602'—Second model
602.sup.N—N'th model
603—Model resolution
701—Mean value
702—Probability distribution
702'—First probability island
702"—Local minima
702'"—Second probability island
702""—Third probability island
703—Transformed parameter measurement distribution.

The invention claimed is:

1. A method for liquid condition assessment in a liquid lubrication system for a work system operable in at least two different operation modes, wherein the method comprises:

measuring monitored liquid condition data;
determining which one of the operation modes the work system comprises;
based on the determined operation mode, selecting from a list of at least two models, one of the models corresponding to the determined operation mode;
modelling simulated liquid condition data that corresponds to the monitored liquid condition data, wherein the simulated liquid condition data is based on the selected model;
assessing a liquid condition of the liquid lubrication system by comparing the monitored liquid condition data with the simulated liquid condition data; and
providing a normally distributed data set for the assessing of the liquid condition.

2. The method of claim 1, wherein the monitored liquid condition data comprises at least one or more wear debris particle readings.

3. The method of claim 1, wherein the monitored liquid condition data comprises at least one of a plurality of liquid degradation readings comprising, wherein the liquid degradation readings comprise at least one of: (a) a temperature reading, (b) a pressure reading, (c) an air content reading, and (d) a humidity reading.

4. The method of claim 1, wherein the liquid lubrication system comprises liquid, and the liquid inside the lubrication system comprises an oil product.

5. The method of claim 1, wherein one of the at least two different operation modes comprises the work system being turned off and where another of the at least two different operation modes comprises the work system being turned on.

6. The method of claim 1, wherein the at least two different operation modes comprise the work system being turned on.

7. The method of claim 1, wherein the liquid lubrication system is configured for a work system on a ship.

8. The method of claim 1, wherein:
the comparison of the monitored liquid condition data with the simulated liquid condition data results in a variance; and
the providing of the normally distributed data set comprises producing the normally distributed data set at least partially based on the variance.

9. An apparatus for liquid condition assessment in a liquid lubrication system for a work system operable in at least two different operation modes, wherein the apparatus comprises:
a first receiver configured to receive monitored liquid condition data;
a second receiver configured to receive information corresponding to one of the operation modes that the work system comprises;
a selector configured to select one of a plurality of models based on one of the operation modes;
a simulator configured to model simulated liquid condition data that corresponds to the monitored liquid condition data, wherein the simulated liquid condition data is based on the selected model;
an assessor configured to assess the liquid condition by comparing the monitored liquid condition data with the simulated liquid condition data; and
a provider configured to provide a normally distributed data set applicable to assess the liquid condition.

10. The apparatus of claim 9, where the first receiver comprises a sensor configured to gather the monitored liquid condition data.

11. The apparatus of claim 9, wherein the first receiver is configured to gather the monitored liquid condition data at a location along an offline filtration system.

12. The apparatus of claim 9, wherein the monitored liquid condition data comprises at least one or more wear debris particle readings.

13. The apparatus of claim 9, wherein the monitored liquid condition data comprises at least one of: (a) a liquid degradation reading, (b) a temperature reading, (c) a pressure reading, (d) an air content reading, and (f) a humidity reading.

14. The apparatus of claim 9, wherein the liquid lubrication system comprises liquid, and the liquid inside the lubrication system comprises an oil product.

15. The apparatus of claim 9, wherein one of the at least two different operation modes comprises the work system being turned off, and another one of the at least two different operation modes comprises the work system being turned on.

16. The apparatus of claim 9, wherein the apparatus is configured and operable to assess the liquid lubrication system for a work system on a ship.

17. The apparatus of claim 9, wherein:
the comparison of the monitored liquid condition data with the simulated liquid condition data results in a variance; and
the normally distributed data set is at least partially based on the variance.

* * * * *